United States Patent [19]
Foster

[11] Patent Number: 5,011,476
[45] Date of Patent: Apr. 30, 1991

[54] SINGLE FILL AND USE SYRINGE

[76] Inventor: Robert J. C. Foster, 6 Glasson Square, Mt. Waverley, Australia

[21] Appl. No.: 455,419
[22] PCT Filed: Jun. 30, 1988
[86] PCT No.: PCT/AU88/00230
    § 371 Date: Dec. 28, 1989
    § 102(e) Date: Dec. 28, 1989
[87] PCT Pub. No.: WO89/00057
    PCT Pub. Date: Jan. 12, 1989

[30] Foreign Application Priority Data
    Jul. 2, 1987 [AU] Australia ............... PI2840

[51] Int. Cl.[5] ............................................. A61M 5/00
[52] U.S. Cl. ................................. 604/110; 604/220
[58] Field of Search ............... 604/110, 218, 220, 221

[56] References Cited

U.S. PATENT DOCUMENTS

| | | |
|---|---|---|
| 1,863,785 | 6/1932 | Dickinson ................... 604/220 |
| 2,373,520 | 4/1945 | Wallin ........................ 604/210 |
| 3,951,146 | 4/1976 | Chiquiar-Arias . |
| 3,998,224 | 12/1976 | Chiquiar-Arias . |
| 4,030,498 | 6/1977 | Tompkins ................. 604/221 X |
| 4,391,272 | 7/1983 | Staempfli ...................... 604/110 |
| 4,731,068 | 3/1988 | Hesse ........................... 604/110 |

FOREIGN PATENT DOCUMENTS

| | | | |
|---|---|---|---|
| 2181580 | 4/1972 | France . | |
| 2204429 | 10/1973 | France . | |
| 580185 | 8/1946 | United Kingdom | ............ 604/220 |

Primary Examiner—John D. Yasko
Attorney, Agent, or Firm—Kinney & Lange

[57] ABSTRACT

It is an object of the present invention to provide a syringe which is as cheap to manufacture as the standard plastic disposable syringe but which cannot conveniently be reused after it is filled and used once.

The syringe comprises a cylindrical barrel (2) and inside the barrel (2) a cylindrical plunger (9) with a resilient base (10) in sealing relation with the barrel (2), the plunger (9) having at least one circumferential groove (13a) and the barrel having an inwardly extending circumferential projection (11) around its aperture (8) such that the projection (11) engages the groove (13a) to prevent withdrawal of the plunger (9).

2 Claims, 1 Drawing Sheet

SINGLE FILL AND USE SYRINGE

TECHNICAL FIELD

This invention relates to syringes and more particularly to medical syringes which can only be used once.

BACKGROUND ART

Medical syringes comprise a cylindrical barrel and a plunger with a cylindrical base made of resilient material located in sealing relation within the barrel and a needle mounted at the base of and in communication with the barrel.

Originally the barrel was made of glass and the syringe was designed for multiple use with either the needle or the whole syringe being subjected to sterilisation between uses. However, for convenience and in order to minimize cross infection, the syringes most used in medicine now are plastic disposables.

Although relatively cheap and disposable, these syringes can be reused and usually are by drug users amongst whom the spread of Acquired Immune Deficiency Syndrome (AIDS) is on the increase because of the sharing of syringes.

Many prior art syringes have been designed in an attempt to prevent reuse. Some use complicated mechanisms to prevent withdrawal of the plunger; these are difficult to manufacture and greatly increase the cost over the plastic disposable. Others use techniques in which the plunger collapses or the seal between the plunger and the barrel is broken, which prevents suction. None of these have proved to be reliable and affordable and although medically desirable have not been successful.

DISCLOSURE OF INVENTION

It is an object of the present invention to provide a syringe which is as cheap to manufacture as the standard plastic disposable syringe but which cannot conveniently be reused after it is filled and used once.

This invention comprises a syringe having a cylindrical barrel and inside the barrel a cylindrical plunger with a resilient base in sealing relation with the barrel, the plunger having at least one circumferential groove and the barrel having an inwardly extending circumferential projection at its aperture such that the projection engages the groove to prevent withdrawal of the plunger.

In a preferred form of the syringe of this invention the plunger has one groove located so that engagement with the projection on the barrel occurs when the plunger is pressed home fully and a second groove located between the first groove and the base so that engagement with the projection occurs before the plunger is pressed home fully.

BRIEF DESCRIPTION OF THE DRAWINGS

Following is a description of a preferred embodiment of the invention with reference to the drawings in which.

BEST MODE FOR CARRYING OUT THE INVENTION

Figure 1:
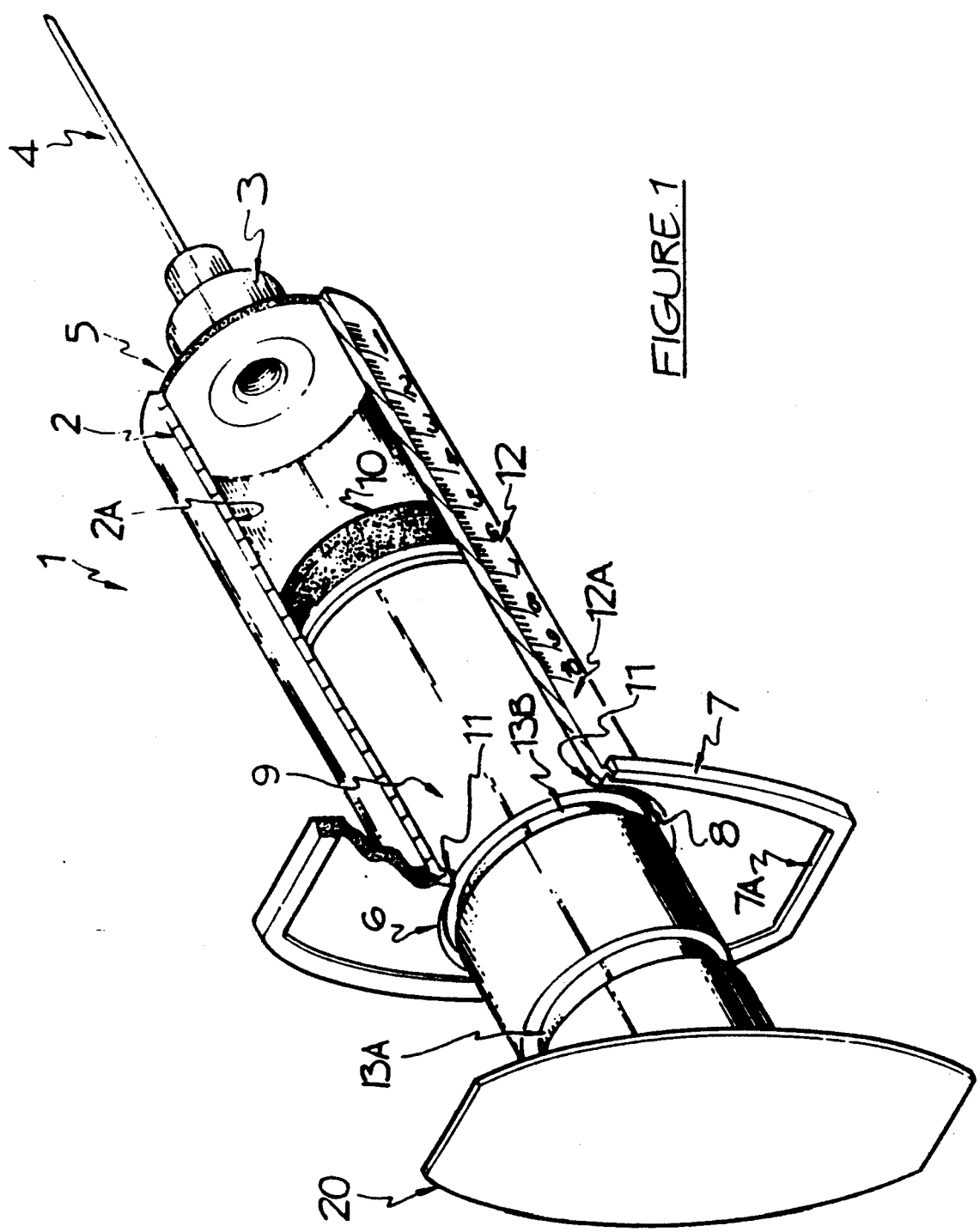
FIG. 1 is a perspective view of a syringe with part of the barrel cut away.

The syringe 1 consists of a barrel 2 having a needle assembly 3, including a non-removable needle 4 at its end 5. The other end 6 of the barrel 2 has an oblong flange 7 serving as a finger support around aperture 8.

Extending through aperture 8 is a cylindrical plunger 9 with a base 10 made of resilient material in air-tight relation with the inner barrel wall 2a such that withdrawal of the plunger 9 will result in the inward suction of liquid through the needle 4. Plunger 9 is provided with two annular grooves 13a and 13b adjacent to its outer end and the inner wall 2a of barrel 2 has an annular barb 11 located adjacent to its outer extremity. Plunger 9 is further provided at its outer end with a flange 20 adapted to sit within a recess 7a of flange 7 when the base 10 bottoms on end 5 of the barrel.

The syringe is supplied to the user with the plunger 9 partially withdrawn so that groove 13b is just outside the barrel 2. The user fills the syringe 1 by withdrawing the plunger 9 to the full extent of the barrel while the needle is inserted in the liquid to be injected.

The barrel has a portion 12a which is additional to the measured dose and greater than the travel of the plunger between grooves 13a 13b. This allows the full measured dose viz. 10 mls to be drawn into the syringe without the groove 13b passing into engagement with the barb 11 of the barrel.

The syringe is asperated by pushing the plunger 9 until the base 10 is level with the dosage mark required and then the liquid injected by pushing the plunger home. After groove 13b passes barb 11 it will be impossible to withdraw the plunger because of the locking engagement of the barb in the groove for the reverse direction of motion.

The barrel can be extended and the groove 13b can be located so that this engagement occurs when between 50% and 90% of the dose has been injected. Preferably, engagement occurs when 70% of the dose has been injected. Accordingly it is not possible to inject more than 70% of the dose and still reuse the syringe.

Further, when the plunger (9) is pushed home fully, the flange 20 sits within the recess 7a of flange 7. In this position it is difficult to obtain purchase on the plunger in an attempt to force withdrawal from its locking engagement with the barrel.

I claim:

1. A syringe (1) having a cylindrical barrel (2) and inside the barrel (2) a cylindrical plunger (9) with a resilient base (10) in sealing relation with the barrel (2), the plunger (9) having a first circumferential groove (13a) and designed to engage an inwardly extending circumferential projection (11) disposed about the barrel (2) around its aperture (8) such that the first groove (13a) engages the projection (11) to prevent withdrawal of the plunger (9) when base (10) bottoms on the end (5) of the barrel (2) and the plunger (a) having a second groove (13b) designed to engage the projection (11) before the plunger (9) is pressed home and with the barrel having (2) a portion (12a) which is additional to a measured dose and greater than the travel of the plunger (9) between grooves (13a) and (13b).

2. The syringe of claim 1 in which the travel of the plunger (9) between the grooves (13a) and (13b) is equivalent to 30% of the measured dose.

* * * * *